United States Patent [19]

Isasi Capelo et al.

[11] Patent Number: 4,890,629

[45] Date of Patent: Jan. 2, 1990

[54] HUMAN CENTRIFUGATION MACHINE

[76] Inventors: Elida S. Isasi Capelo; María E. Isasi Capelo, both of Arenal Grande 2777 St., Montevideo, Uruguay

[21] Appl. No.: 61,230

[22] Filed: Jun. 8, 1987

[30] Foreign Application Priority Data

Jun. 6, 1986 [UY] Uruguay ................................ U2249
Mar. 25, 1987 [AR] Argentina ............................. 307110

[51] Int. Cl.$^4$ ............................................ A61M 21/00
[52] U.S. Cl. .................................................... 128/897
[58] Field of Search ........................ 128/1 A, 1 R, 1 C; 272/16, 17, 28 R; 434/30, 34, 35

[56] References Cited

U.S. PATENT DOCUMENTS 3,010,219 11/1961 Schneller ............................ 434/34
3,136,075 6/1964 Brian ..................................... 434/34
3,216,423 11/1965 Blonsky et al. ..................... 178/361
4,386,613 6/1983 Locsei ................................ 128/1 R

OTHER PUBLICATIONS

Science News Letter, Oct. 3, 1942.

*Primary Examiner*—Ruth S. Smith
*Assistant Examiner*—J. P. Lacyk
*Attorney, Agent, or Firm*—Lackenbach Siegel Marzullo & Aronson

[57] ABSTRACT

A centrifugation machine for medical treatment of humans includes a plurality of support arms whereon a patient is restrained by straps, railings and footrests with his head adjacent the center of rotation. The patient is restrained in a supine position or by means of a truncated pyramid shaped accessory mounted at the center of rotation, the patient may be restrained in a half-seat position. Twenty g forces can be applied.

5 Claims, 3 Drawing Sheets

HUMAN CENTRIFUGATION MACHINE

BACKGROUND OF THE INVENTION

This invention refers to a utility model called "HUMAN CENTRIFUGATION MACHINE", more specifically to a functional constructive innovation, featuring a new structure and arrangement of elements which make it possible to take full advantage of them and obtain results from the use for which they are intended.

The development of aerospace systems capable of bringing about high levels of stress of +g has given rise to the necessity (on the part of a number of scientists) of looking into the cardiovascular system responses to acceleration and deceleration.

As far back as 1795, Erasmus Darwin, a physicist of that time endowed with imagination, was already toying with the idea of centrifugation to induce sleep, reduce heart activity and suppress fever.

Centrifugation was used during the nineteenth century in Europe for mental ailments. Subsequently, at the beginning of the twentieth century, it was recognized that the gravity accelerating forces and centrifugation exerted identical effects on the human body.

Centrifugation became then an ideal, practical and safe system to look into man's response to acceleration changes. This was supported in the past few years by the quick development of aviation, boosted by the two world wars, and by the arrival of the space age.

For decades, centrifugation was used for therapeutical purposes in neurosurgery to displace a bullet lodged in the brain (1970), or as a treatment for high blood pressure (1949, before the employment of rauwolfia) and for arteriopathy of the lower limbs (1950).

However, it was difficult to conceive a new device based on mechanical principles be applied and approved in support of different therapies. For many years now (since 1976) we have been carrying out a lot of clinical observations into the effect of centrifugation on the arterial vascular system of normal volunteers and patients suffering from arteritis, patients who were carriers of lymphedema, etc. Each of these findings prompted us to look for non-invasive techniques which could establish with documentary evidence and prove that these clinical observations were a reality. Therefore, we introduced ourselves in the field of Digital Photoplethysmography and Nuclear Medicine, whereupon a new therapy conception unfolded before our eyes.

The device being introduced by us permits one to achieve improved results for its intended purpose, as opposed to any other previously known devices.

Consequently, on account of its structure and arrangement of parts, the device designed here exerts, on the human being subjected to it, effects that are superior to everything known so far, as described below.

For a better understanding of the following explanation, we have added diagrams based upon one of the preferred embodiments of our invention. Obviously, as these diagrams are not intended to represent the invention, it will not be possible to use them in any attempt to restrict the real scope of the protection being requested. This scope is to be determined in accordance with the law and practice in force in this regard, with the help of the list of claims attached hereto for such a purpose.

The enclosed drawings show the following details of the particular embodiment selected to this end:

BRIEF DESCRIPTION OF THE DRAWINGS

Other advantages of the invention are described with reference to exemplary embodiments, which are intended to explain and not to limit the invention, and are illustrated in the drawings in which:

FIG. 8 is a perspective view showing the accessory piece mounted onto the primary structure.

DESCRIPTION OF THE PREFERRED EMBODIMENT

Figure 2:
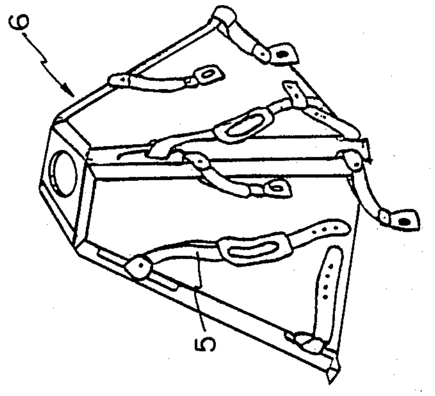
FIG. 2 shows a perspective view of the accessory piece required on some occasions, as described below.
Figure 1:
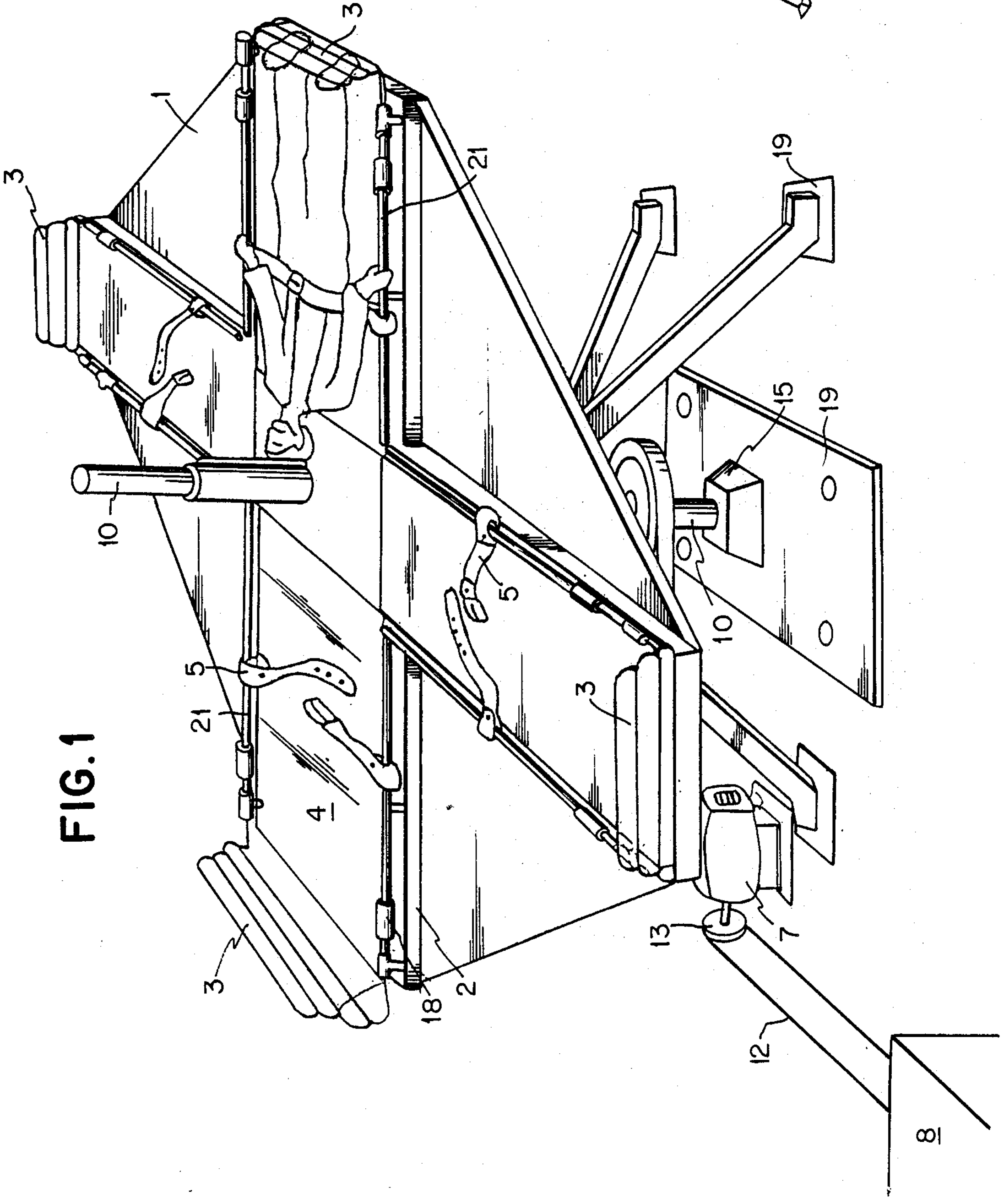
FIG. 1 shows a perspective view of the human centrifugation machine being introduced by us, where it is possible to see its component parts and the position of the patient subjected to it.
Figure 4:
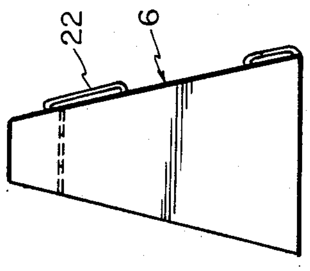
FIG. 4 is a side elevation view of the above mentioned accessory piece.
Figure 5:
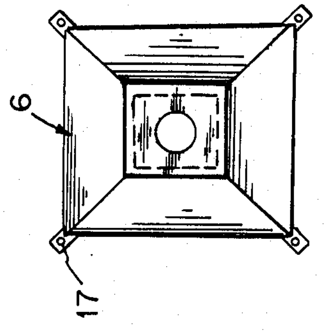
FIG. 5 is a bottom plan view of the accessory piece in question.
Figure 3:
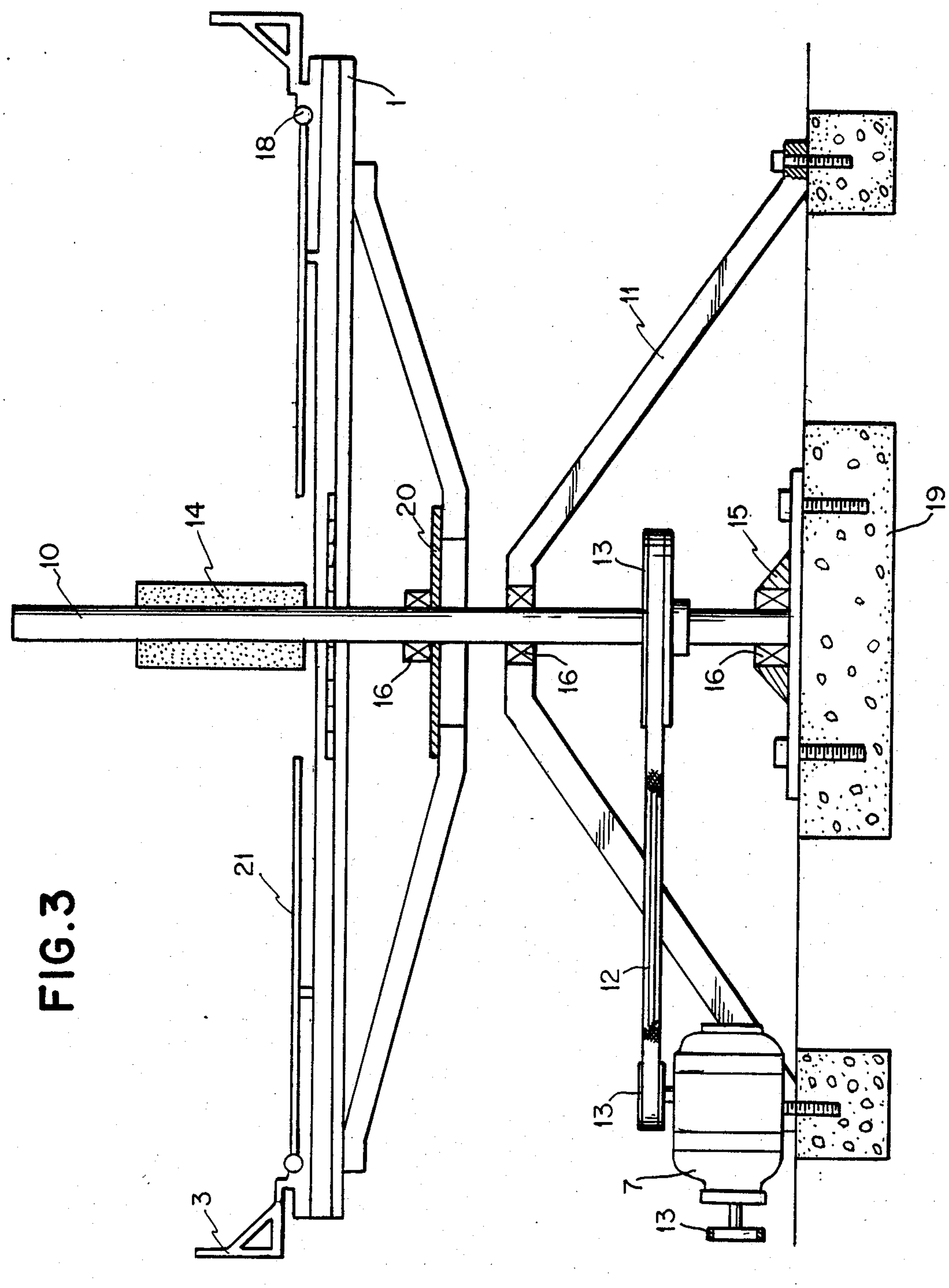
FIG. 3 is a radial elevation cutaway view of the centrifugation machine.
Figure 7:
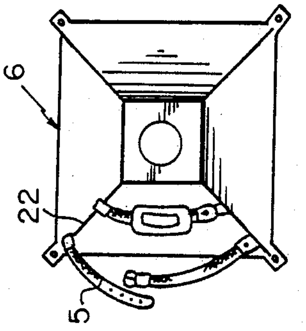
FIG. 7 is an upper plan view of the accessory piece.
Figure 6:
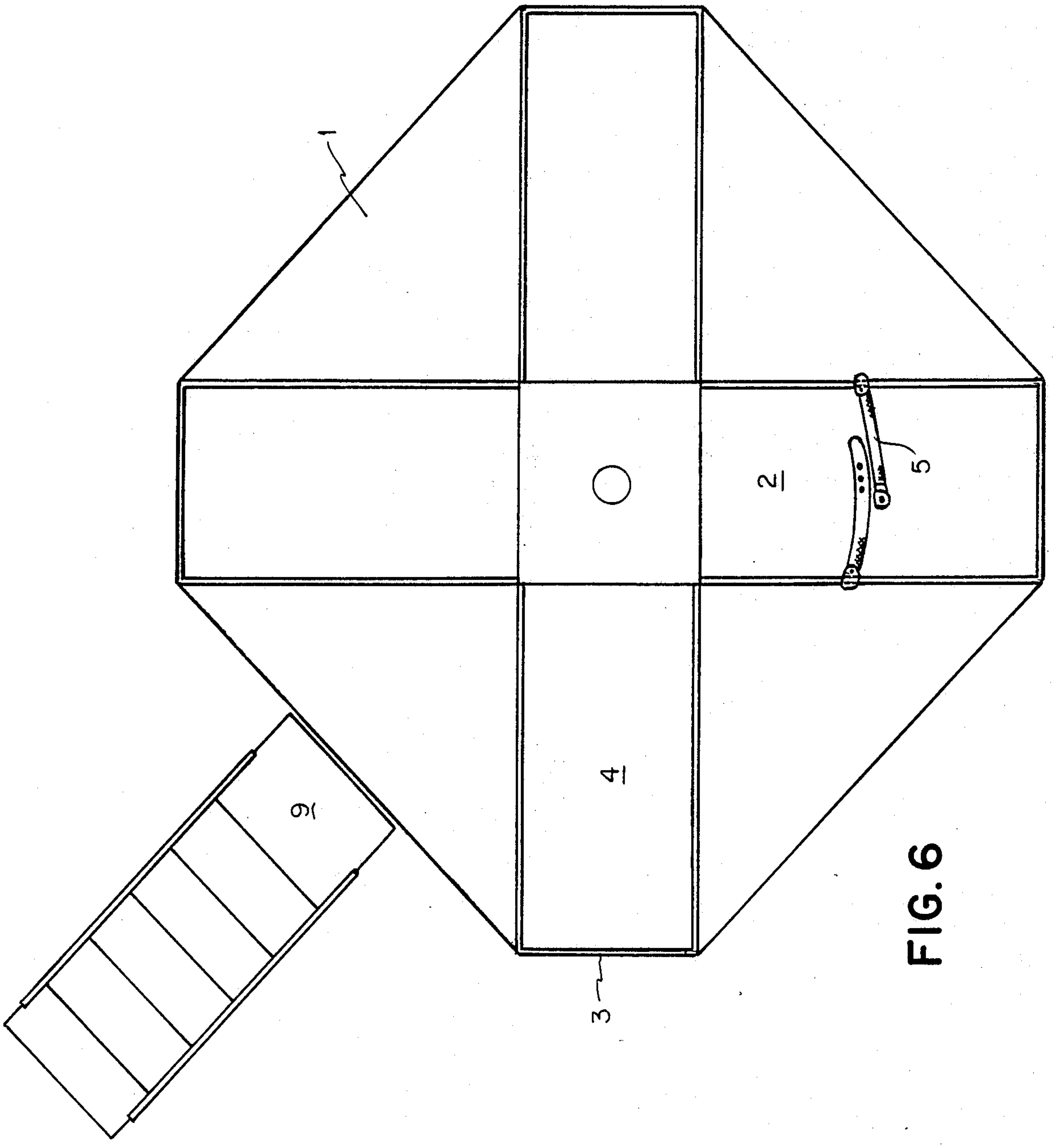
FIG. 6 is an upper plan view with portions omitted of the main device.

Although a specific embodiment of the invention will now be described with reference to the drawings, it should be understood that the embodiment shown is by way of example only and merely illustrative of but one of the many possible specific embodiments which can represent applications of the principals of the invention. Various changes and modifications, obvious to one skilled in the art to which the invention pertains, are deemed to be within the spirit, scope and contemplation of the invention as further defined in the appended claims.

Summing up, our creation is a human centrifugation machine made up of a sheet-metal-covered revolving platform (1), on which there are four stretchers or first support means (2) radially arranged in the form of a cross, over a horizontal plane. Each stretcher or first support means is fitted with two lateral safety railings (21) which enable the patient to hold on, a footrest (3) adjustable in accordance with the patient's height by a length regulating mechanism adjusting screw 18, and safety belts (5).

It is thus possible to select patients with a similar pathology and the same tolerance to the acceleration profiles imposed, in such a way that they may be spun simultaneously. The main feature of this design consists of placing the patient in a supine decubitus position (lying down face upwards), with his or her head resting adjacent the rotating shaft. Such a position (unlike the other one which was half-seated) permits a better tolerance of the encephalic system. The patient in this position bears so well the different acceleration levels that the feeling of rotation goes practically unnoticed, thus avoiding unconfortable feelings such as dizziness or loss of consciousness due to a drop in the encephalic flow."

We therefore deem it essential in this design to place the patient in a supine decubitus position with his or her head resting adjacent the rotating shaft.

If required by the patient's condition, there exists the possibility of resorting to the half-seated position. For this purpose, a truncated-pyramid-shaped accessory piece or second support means (6) is fitted, enabling the patient to lean his or her back against one of the pyramid faces. The accessory piece 6 is provided with safety belts holders 22 and safety belts 5.

The revolving platfrom 1 is positioned on a plurality of legs 11 and provided with a vertical shaft 10. The revolving platform 1 and the shaft 10 are rotatable within bearing units 20 having bearings 16 and within a thrust bearing 15. The thrust bearing 15 as well as the legs 11 are supported by a foundation 19. The platform 1 is rotated by an electric motor (energized via a control table 8) through a speed reducer 7, interconnecting V-belts 12 and associated pulleys 13. During rotation of the revolving platform it is possible to obtain a maximum recommended acceleration of 20 g.

The centrifugal force is exerted in a cephalo-podalic direction (+g), the patient in a supine decubitus position becoming a radius of the revolving platform.

In order to determine in advance the centrifugation tolerance individually, patients were exposed to different acceleration and deceleration levels, beginning with 1-2 g and applying gradual increases until reaching 6 g.

The g acceleration applied gradually is obtained in five-minute centrifugation session, the maximum speed is reached in one minute, the speed level is then kept for three minutes and, finally, it is decelerated in one minute until the revolving speed is equal to zero.

We claim:

1. A human centrifugation machine comprising a shaft mounted for rotation about its longitudinal axis;

a plurality of first support means connected to said shaft for rotation therewith and extending radially of said shaft and transversely to said axis, said plurality of first support means adapted to at least partially support at least two humans during rotation;

restraint means for holding each human respectively in position on one of said first support means during rotation;

second support means removably attached to said first support means, said second support means when attached providing a plurality of sloped surfaces, each said sloped surface extending from each said first support means toward said shaft and being acutely angled relative to both said shaft and each said first support means, each human being positioned either to lie in a supine position on one of said first support means with the head of said human adjacent said shaft when said second support means is removed, or being positioned on one of said first support means in a half-seated position with said second support means attached, the back of the human from hips upward resting against one of said sloped surfaces, the rear end and feed of said human being supported by one of said first support means; and means for rotating said shaft.

2. A human centrifugation machine as claimed in claim 1, wherein the number of said first support means is four, said first support means being arranged in a cross, and the number of said sloped surfaces on said second support means being four.

3. A human centrifugation machine as claimed in claim 1, wherein said means for rotating said shaft includes means for providing at least a 20 g rotational acceleration.

4. A human centrifugation machine as claimed in claim 1, wherein said restraint means includes straps and side railings attached to footrests and said first support means, said footrests being individually radially positionable relative to said shaft whereby the height of the human is accommodated.

5. The machine as claimed in claim 1, wherein said second support means further includes supplemental restraint means attached to said sloped surfaces.

* * * * *